United States Patent
Doan et al.

(10) Patent No.: US 10,226,627 B2
(45) Date of Patent: Mar. 12, 2019

(54) PRIMING NEUROMODULATION FOR FASTER THERAPEUTIC RESPONSE

(71) Applicant: Boston Scientific Neuromodulation Corporation, Valencia, CA (US)

(72) Inventors: Que T. Doan, West Hills, CA (US); Bradley Lawrence Hershey, Valencia, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 198 days.

(21) Appl. No.: 15/141,075

(22) Filed: Apr. 28, 2016

(65) Prior Publication Data

US 2016/0317815 A1    Nov. 3, 2016

Related U.S. Application Data

(60) Provisional application No. 62/294,762, filed on Feb. 12, 2016, provisional application No. 62/154,556, filed on Apr. 29, 2015.

(51) Int. Cl.
*A61N 1/00* (2006.01)
*A61N 1/36* (2006.01)
(Continued)

(52) U.S. Cl.
CPC ....... *A61N 1/36071* (2013.01); *A61N 1/0551* (2013.01); *A61N 1/3615* (2013.01);
(Continued)

(58) Field of Classification Search
CPC .............. A61N 1/36071; A61N 1/0551; A61N 1/36135; A61N 1/3615; A61N 1/37241; A61N 1/37247
See application file for complete search history.

(56) References Cited

U.S. PATENT DOCUMENTS

| | | | |
|---|---|---|---|
| 5,292,340 A | | 3/1994 | Crosby et al. |
| 5,775,331 A | * | 7/1998 | Raymond ................ A61N 1/05 600/554 |

(Continued)

FOREIGN PATENT DOCUMENTS

| | | |
|---|---|---|
| WO | WO-9639932 A1 | 12/1996 |
| WO | WO-2016176425 A1 | 11/2016 |

OTHER PUBLICATIONS

"International Application Serial No. PCT/US2016/029735, International Preliminary Report on Patentability dated Nov. 9, 2017", 6 pgs.

(Continued)

*Primary Examiner* — Lindsey G Wehrheim

(74) *Attorney, Agent, or Firm* — Schwegman Lundberg & Woessner, P.A.

(57) ABSTRACT

An example a system includes a neuromodulation generator that may be configured to use electrodes to generate a first modulation field over a test region of neural tissue along the electrodes to prime the neural tissue throughout the test region and a second modulation field to test targeted locations within the test region for therapeutic effectiveness. A memory may be configured to store a first modulation field parameter for generating the first modulation field and a second modulation field parameter set for generating the second modulation field to modulate a targeted location within the test region. The second modulation field parameter set is programmable for modulating other targeted locations. The controller may be configured to control the neuromodulation generator to use the first modulation field parameter set to deliver the first modulation field and to use the second modulation field parameter set to deliver the second modulation field.

20 Claims, 12 Drawing Sheets

(51) Int. Cl.
*A61N 1/05* (2006.01)
*A61N 1/372* (2006.01)

(52) U.S. Cl.
CPC ..... *A61N 1/36135* (2013.01); *A61N 1/37241* (2013.01); *A61N 1/37247* (2013.01)

(56) References Cited

U.S. PATENT DOCUMENTS

| | | |
|---|---|---|
| 8,412,345 B2 | 4/2013 | Moffitt |
| 2011/0054564 A1 | 3/2011 | Valencia |
| 2013/0204315 A1 | 8/2013 | Wongsarnpigoon et al. |
| 2013/0282078 A1 | 10/2013 | Wacnik |
| 2015/0032181 A1 | 1/2015 | Baynham et al. |
| 2016/0271413 A1 | 9/2016 | Vallejo et al. |
| 2017/0348530 A1 | 12/2017 | Doan et al. |
| 2017/0348535 A1 | 12/2017 | Doan et al. |
| 2017/0348540 A1 | 12/2017 | Doan et al. |

OTHER PUBLICATIONS

"International Application Serial No. PCT/US2016/029735, International Search Report dated Jul. 12, 2016", 3 pgs.
"International Application Serial No. PCT/US2016/029735, Written Opinion dated Jul. 12, 2016", 4 pgs.
"U.S. Appl. No. 15/610,839, Non Final Office Action dated Jun. 29, 2018", 18 pgs.
"U.S. Appl. No. 15/611,068, Response filed Jul. 11, 2018 to Restriction Requirement Action dated Jun. 15, 2018", 5 pgs.
"U.S. Appl. No. 15/611,068, Restriction Requirement dated Jun. 15, 2018", 6 pgs.
"European Application Serial No. 16720690.3, Response filed Aug. 3, 2018 to Communication Pursuant to Rules 161(2) and 162 EPC dated Feb. 7, 2018", 12 pgs.

\* cited by examiner

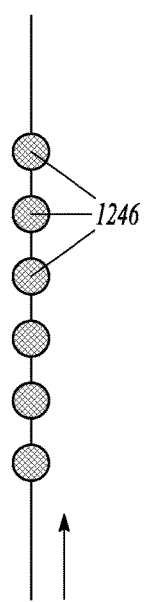 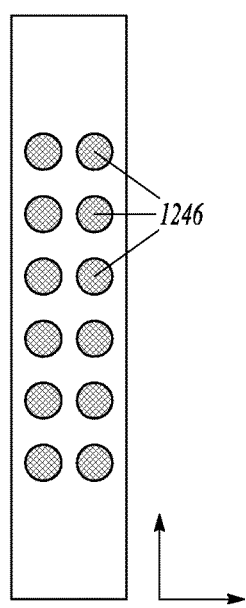 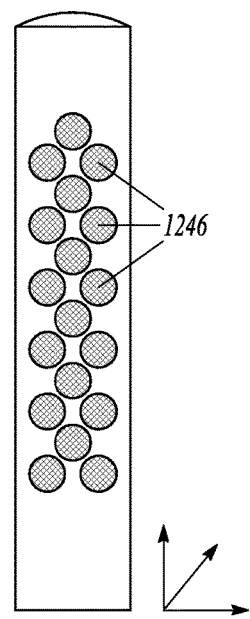
*FIG. 12A*  *FIG. 12B*  *FIG. 12C*

PRIMING NEUROMODULATION FOR FASTER THERAPEUTIC RESPONSE

CLAIM OF PRIORITY

This application claims the benefit of priority to U.S. Provisional Patent Application Ser. No. 62/294,762, filed on Feb. 12, 2016 and U.S. Provisional Patent Application Ser. No. 62/154,556, filed Apr. 29, 2015, each of which is incorporated herein by reference in its entirety.

TECHNICAL FIELD

This document relates generally to medical devices, and more particularly, to systems, devices and methods for delivering neuromodulation.

BACKGROUND

Neuromodulation (or "neural modulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

Conventional SCS delivers electrical pulses to the spinal cord, masking the transmission of pain signals to the brain. While these electrical pulses can reduce pain, they are often associated with possible unpleasant tingling and buzzing sensations known as paresthesia.

Sub-perception SCS therapy has been proposed to provide pain relief without the accompanying paresthesia. However, the wash-in time for sub-perception SCS therapy is significant. The wash-in time refers to a time from the start of a therapy to when a therapeutic response to the therapy can be observed. Since there typically is no immediate feedback for a sub-perception SCS, it can be a challenge to find a desirable or optimal location (sweet-spot) for the modulation field within an office visit.

SUMMARY

An example (e.g., "Example 1") of a system includes an electrode arrangement, a neuromodulation generator, a memory, and a controller. The neuromodulation generator may be configured to use electrodes in the electrode arrangement to generate modulation fields including a first modulation field over a test region of neural tissue along the electrode arrangement to prime the neural tissue throughout the test region, and a second modulation field to test a plurality of targeted locations of neural tissue within the test region for therapeutic effectiveness. The memory may be configured to store a first modulation field parameter set for use to generate the first modulation field, and a second modulation field parameter set for use to generate the second modulation field to modulate one of the plurality of the targeted locations within the test region. The second modulation field parameter set is programmable to change the second modulation field to modulate other ones of the plurality of targeted locations. The controller may be configured to control the neuromodulation generator to use the first modulation field parameter set to prime the test region with the first modulation field and to use the second modulation field parameter set to deliver a second modulation field to modulate the one of the targeted locations within the test region.

In Example 2, the subject matter of Example 1 may optionally be configured such that the neuromodulation generator is configured to use electrodes in the electrode arrangement to generate at least one sub-perception modulation field, and at least one of the first modulation field and the second modulation field is the sub-perception modulation field.

In Example 3, the subject matter of Example 1 may optionally be configured such that the neuromodulation generator is configured to use electrodes in the electrode arrangement to generate at least one supra-perception modulation field, and at least one of the first modulation field and the second modulation field is the supra-perception modulation field.

In Example 4, the subject matter of any one or any combination of Examples 1-3 may optionally be configured such that the controller is configured to generate the first modulation field to prime the test region for a period of time before the second modulation field.

In Example 5, the subject matter of any one or any combination of Examples 1-3 may optionally be configured such that the controller is configured to generate the first modulation field for at least a portion of a time when the second modulation field is generated.

In Example 6, the subject matter of any one or any combination of Examples 1-5 may optionally be configured such that the controller is configured to implement a trolling routine to troll the second modulation field through the plurality of targeted locations within the test region of neural tissue.

In Example 7, the subject matter of Example 6 may optionally be configured such that the trolling routine implemented by the controller is configured to perform at least one of automatically moving the second modulation field or receiving a user-controlled trolling command to control movement of the second modulation field.

In Example 8, the subject matter of Example 8 may optionally be configured such that the programmable second modulation field parameter set includes programmable fractionalized current values for electrodes within the electrode arrangement, wherein modification of the programmable fractionalized current values moves the second modulation field.

In Example 9, the subject matter of any one or any combination of Examples 6-8 may optionally be configured such that the controller is configured to implement a routine as the second modulation field is trolled through the plurality of targeted positions within the test region to identify one or more therapeutically-effective locations in the test region where the second modulation field provides pain relief, and to store in the memory the modulation field parameter data that provides the pain relief as the second modulation field parameter set and measures indicating therapeutic effectiveness for each location of the plurality of targeted positions.

In Example 10, the subject matter of Example 9 may optionally be configured such that the one or more therapeutically-effective locations includes a tested location within the test region of neural tissue that is most effective in providing pain relief.

In Example 11, the subject matter of Example 10 may optionally be configured such that the neuromodulation generator is configured to prime a target region over the therapeutically-effective location and deliver a therapeutic modulation to the therapeutically-effective location.

In Example 12, the subject matter of any one or any combination of Examples 9-11 may optionally be configured such that the routine implemented by the controller is configured to receive a titration signal that indicates an instruction to adjust an intensity of the second modulation field, adjust the intensity in response to receiving the titration signal, and receive an indication signal that the adjusted modulation intensity achieved the pain relief.

In Example 13, the subject matter of Example 12 may optionally be configured such that the titration signal includes an automatically-provided signal to automatically adjust the intensity of the second modulation field, and the system is configured to receive a user-provided command to stop the automatic adjustment of the intensity of the second modulation field.

In Example 14, the subject matter of any one or any combination of Examples 1-13 may optionally be configured such that the controller is configured to use a timing channel to prime the test region and to use at least one other timing channel to generate to deliver the therapeutic modulation.

In Example 15, the subject matter of any one or any combination of Examples 1-14 may optionally be configured such that the system includes an implantable device and an external device. The implantable device includes the neuromodulation generator, the memory and the controller. The external device and the implantable device are configured to communicate. The external device is configured to provide a graphical user interface to provide at least one of a graphical lead indicator configured to indicate the test region of neural tissue or at least one of the plurality of the targeted locations within the test region.

An example of a method (e.g., "Example 16") is also provided. The method may include generating a first modulation field over a test region of neural tissue along an electrode arrangement to prime the neural tissue throughout the test region, and generating a second modulation field to test a plurality of targeted locations of neural tissue within the test region for therapeutic effectiveness.

In Example 17, the subject matter of Example 16 may optionally include that at least one of the first modulation field or the second modulation field includes a sub-perception modulation field.

In Example 18, the subject matter of Example 16 may optionally include that at least one of the first modulation field or the second modulation field includes a supra-perception modulation field.

In Example 19, the subject matter of generating the first modulation field as found in any one or any combination of Examples 16-18 may optionally include generating the first modulation field over the test region of neural tissue along the electrode arrangement to prime the neural tissue throughout the test region for a period of time before generating the second modulation field.

In Example 20, the subject matter of generating the first modulation field as found in any one or any combination of Examples 16-18 may optionally include generating the first modulation field for at least a portion of a time when the second modulation field is generated.

In Example 21, the subject matter of any one or any combination of Examples 16-20 may optionally further include trolling the second modulation field through the plurality of targeted locations within the test region of neural tissue. The trolling includes automatically moving the second modulation field or receiving a user-controlled trolling command to control movement of the second modulation field.

In Example 22, the subject matter of generating the second modulation field as found in any one or any combination of Examples 16-21 may optionally include using a programmable second modulation field parameter set to generate the second modulation field to modulate one of the plurality of the targeted locations within the test region.

In Example 23, the subject matter of Example 22 may optionally further include programming different values for the programmable second modulation field parameter set to move the second modulation field to different ones of the plurality of targeted locations within the test region of neural tissue.

In Example 24, the subject matter of Example 23 may optionally further include identifying a therapeutically-effective location being a tested location of the plurality of targeted locations within the test region of neural tissue that is most effective in treating a condition using a therapeutic modulation.

In Example 25, the subject matter of Example 24 may optionally further include priming a target region over the therapeutically-effective location and delivering the therapeutic modulation to the therapeutically-effective location.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 12A-12C illustrate, by way of example and not limitation, neural tissue locations that may be targeted within the test region in one, two and three dimensions, respectively.

DETAILED DESCRIPTION

Figure 1:
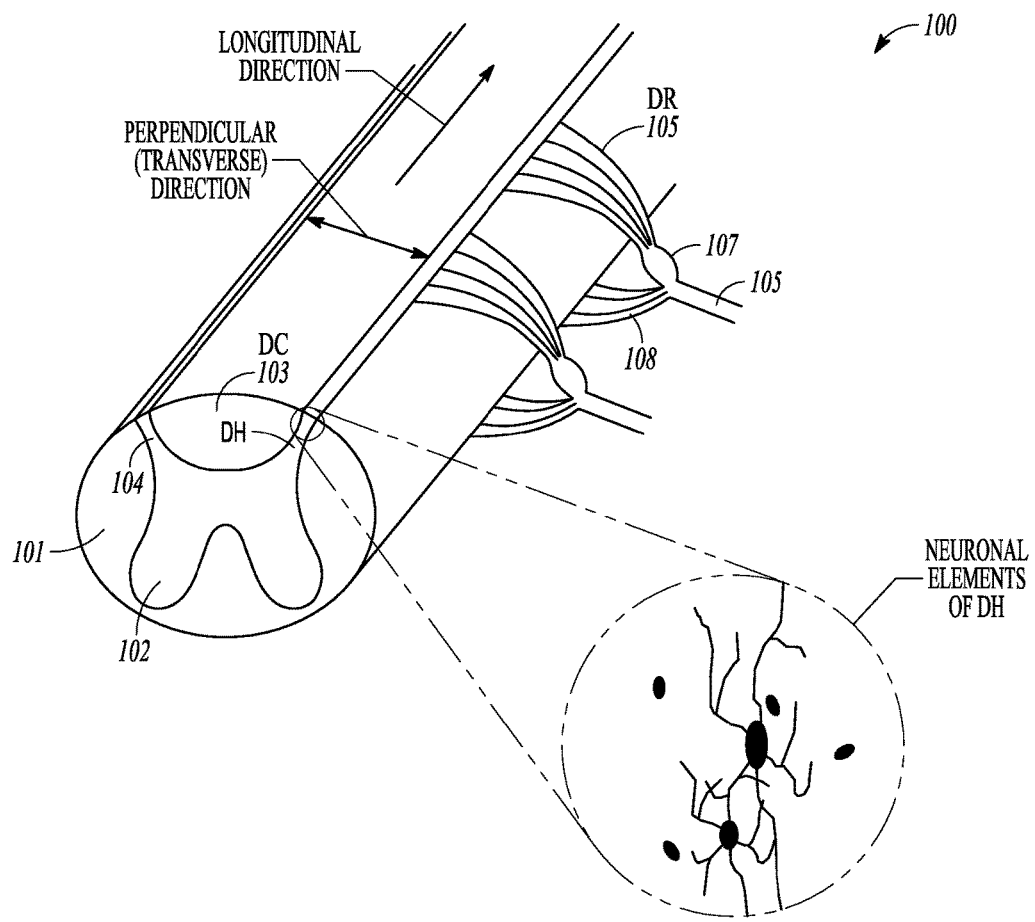
FIG. 1 illustrates a portion of a spinal cord.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Sub-perception neuromodulation is neuromodulation that can be therapeutically effective. Thus, the therapeutic effects of the sub-perception neuromodulation can be perceived. However, unlike conventional SCS therapy which can cause sensations (e.g. paresthesia) when the therapy is delivered, the energy of the delivered sub-perception modulation field is not perceptible. That is, a patient is not able to sense when the stimulation is "on" or "off".

Sub-perception SCS may typically have a wash-in period on the order of about one day. Thus, when the programmed modulation parameters are changed to change the location of the modulation field, the patient may not be able to determine the effect that the changes have on pain for a day or so. This make it difficult quickly titrate the modulation field of the sub-perception SCS to provide effective pain relief to the patient.

Various embodiments may be used to provide a faster therapeutic response (e.g. pain relief) to the sub-perception modulation. Faster responses to sub-perception modulation may be useful in order to find an effective location (sweet-spot) for the modulation field within an office visit. The sweet spot may be a relatively optimal location for the modulation field as it is more optimal than other locations tested.

Various embodiments may deliver a low intensity field in preparation for testing for and finding the sweet-spot for the sub-perception modulation field. The preparatory, lower intensity field may be referred to herein as a prime field, as it is used to prime the neural tissue to induce a faster response to the sub-perception modulation field. Thus, priming the neural tissue enables faster pain relief feedback from the patient during the search for the modulation field sweet spot.

While priming neural tissue for purposes of testing sub-perception modulation is specifically discussed as an example, priming neural tissue can be applied to lower the stimulation energy required for both sub-perception modulation and supra-perception modulation, and expedite the response to both test and therapeutic modulations. The energy of the supra-perception modulation delivered to the modulation field is perceptible. The therapeutic modulation is delivered to treat a condition indicated for at least one type of modulation. A test modulation includes modulation delivered for the purposes of testing effectiveness of a therapeutic modulation and/or setting parameters for the therapeutic modulation. For example, a patient suffering from certain types of pain may be indicated for spinal cord modulation as the therapeutic modulation. A test modulation may be delivered to find the sweet spot for the modulation field and/or other parameters controlling delivery of the therapeutic modulation. Depending on various factors such as patient preference and effectiveness, sub-perception modulation and/or supra-perception modulation may be delivered as the therapeutic modulation. The target tissue of the modulation can be primed for the test modulation and/or the therapeutic modulation. While specifically discussed for test modulation delivered in preparation for therapeutic sub-perception modulation, various embodiments can include applying the priming techniques (including timing of the priming relative to the therapeutic modulation) discussed in this document to test modulation delivered in preparation for therapeutic sub-perception modulation, test modulation delivered in preparation for therapeutic supra-perception modulation, therapeutic sub-perception modulation, and therapeutic supra-perception modulation.

As some embodiments described herein involve Spinal Cord Stimulation (SC S, also referred to as spinal cord modulation), a brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases.

Some embodiments deliver sub-perception therapy that is therapeutically effective to treat pain, for example, but the patient does not sense the delivery of the modulation field (e.g. paresthesia). Sub-perception therapy may be provided using higher frequency modulation (e.g. about 1500 Hz or above) of the spinal cord. Sub-perception modulation may also be provided through modulation field shaping (e.g., using multiple independent current control, or MICC), and temporal shaping of pulse train (e.g., burst, longer pulses). It appears that these higher frequencies may effectively block the transmission of pain signals in the afferent fibers in the DC. Some embodiments herein selectively modulate DH tissue or DR tissue over DC tissue to provide sub-perception therapy. Such selective modulation may be delivered at lower frequencies. For example, the selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

While SCS is specifically discussed as an example of neuromodulation therapy, various embodiments can also include applying the priming techniques including timing of delivery discussed in this document to Peripheral Nerve Stimulation (PNS) therapies. For example, sub-perception PNS may be applied to alleviate pain. Various embodiments include priming the neural tissue at target locations for delivering the neuromodulation where required intensity of the neuromodulation for testing and/or therapeutic purposes may be lowered.

Figure 2:
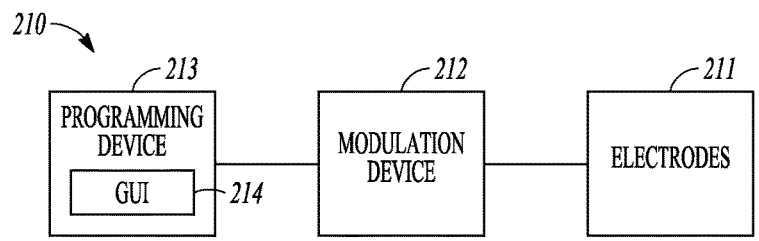
FIG. 2 illustrates, by way of example, an embodiment of a neuromodulation system.

FIG. 2 illustrates an embodiment of a neuromodulation system. The illustrated system 210 includes electrodes 211, a modulation device 212, and a programming device 213. The electrodes 211 are configured to be placed on or near one or more neural targets in a patient. The electrodes 211 may form part of an electrode arrangement. The modulation device 212 is configured to be electrically connected to electrodes 211 and deliver neuromodulation energy, such as in the form of electrical pulses, to the one or more neural targets though electrodes 211. The delivery of the neuromodulation is controlled using a plurality of modulation parameters, such as modulation parameters specifying the electrical pulses and a selection of electrodes through which each of the electrical pulses is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

In various embodiments, the neuromodulation system 210 can include implantable and external elements. For example, the modulation device 212 can be an implantable modulation device, the electrodes 211 can include electrodes in one or more implantable lead and/or the implantable modulation device, and the programming device can be an external programming device configured to be communicatively coupled to the implantable modulation device via telemetry, as further discussed with reference to FIGS. 5 and 6. In another example, the modulation device 212 can be an external modulation device such as a Transcutaneous Electrical Neural Stimulation (TENS) device, the electrodes 211 can include surface electrodes such as skin patch electrodes, and the programming device can be an external programming device configured to be communicatively coupled to the implantable modulation device via a wired or wireless link, or integrated with the external modulation device. In still another example, the modulation device 212 can be an external modulation device, the electrodes 211 can include percutaneous electrodes, and the programming device can be an external programming device configured to be communicatively coupled to the implantable modulation device via a wired or wireless link, or integrated with the external modulation device. In various embodiments, an external modulation device with surface and/or percutaneous electrodes can be used, for example, for delivering a test modulation, delivering a therapeutic modulation during a trial period, and delivering a short-term therapeutic modulation.

In one embodiment, an external modulation device with surface electrodes can be used during a trial period prior to a potential implantation of an implantable SCS system. A skin patch including the surface electrodes is placed over the patient's spine near the region where percutaneous electrodes will be placed for use during the trial period. The external modulation device such as a dedicated External Trial Stimulator (ETC) and/or an external TENS device is used to prime the neural tissue before the trial period using one or more electrodes selected from the surface electrodes. This allows the programming of the external modulation device for delivering therapeutic modulation through the percutaneous electrodes to be performed with reduced wash-in time, such as immediately following the placement of the percutaneous electrodes.

Figure 3:
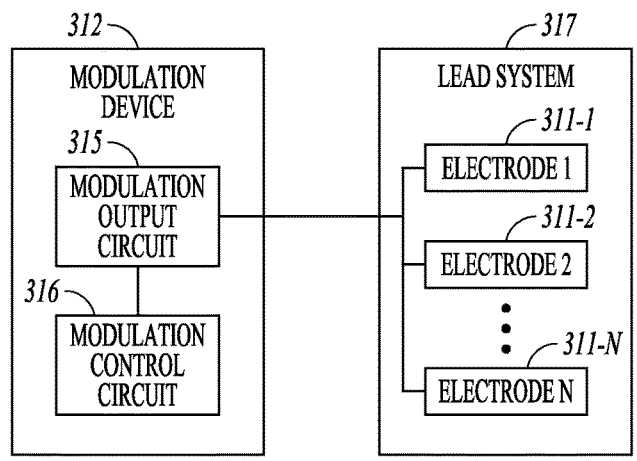
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers neuromodulation pulses. The modulation control circuit 316 controls the delivery of the neuromodulation pulses using the plurality of modulation parameters. The combination of the modulation output circuit 315 and modulation control circuit 316 may collectively be referred to as a pulse generator. The lead system 317 includes one or more leads each configured to be electrically connected to modulation device 312 and a plurality of electrodes 311-1 to 311-N (where N>2) distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical pulses, presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

Conventional programming for SCS therapy uses paresthesia to select an appropriate modulation parameter set. The paresthesia induced by the modulation and perceived by the patient should be located in approximately the same place in the patient's body as the pain that is the target of treatment. When leads are implanted within the patient, an operating room (OR) mapping procedure may be performed to apply electrical modulation to test placement of the leads and/or electrodes, thereby assuring that the leads and/or electrodes are implanted in effective locations within the patient. According to various embodiments, programming for sub-perception modulation may prime the neural tissue to provide faster response times to the sub-perception modulation as part of an OR mapping procedure.

Once the leads are correctly positioned, a fitting procedure, which may be referred to as a navigation session, may be performed to program the external control device, and if applicable the neuromodulation device, with a set of modulation parameters that best addresses the painful site. Thus, the navigation session may be used to pinpoint the volume of activation (VOA) or areas correlating to the pain. The procedure may be implemented to target the tissue during implantation, or after implantation should the leads gradually or unexpectedly move that would otherwise relocate the modulation energy away from the target site. By reprogramming the neuromodulation device (typically by independently varying the modulation energy on the electrodes), the VOA can often be moved back to the effective pain site without having to re-operate on the patient in order to reposition the lead and its electrode array. According to various embodiments, a navigation session for sub-perception modulation may prime the neural tissue to provide faster response times to the sub-perception modulation.

Although various embodiments described in this document prime neural tissue to provide faster responses to sub-perception modulation in order to perform faster OR mapping or navigation sessions, the present subject matter is not limited to such programming. By way of example and not limitation, some embodiment may prime the neural tissue before delivering the sub-perception modulation therapy to the neural tissue simply to reduce the wash-in time of the therapy. Thus, by way of example, a patient may obtain pain relief much quicker with the primed neural tissue than without the primed neural tissue.

Figure 4:
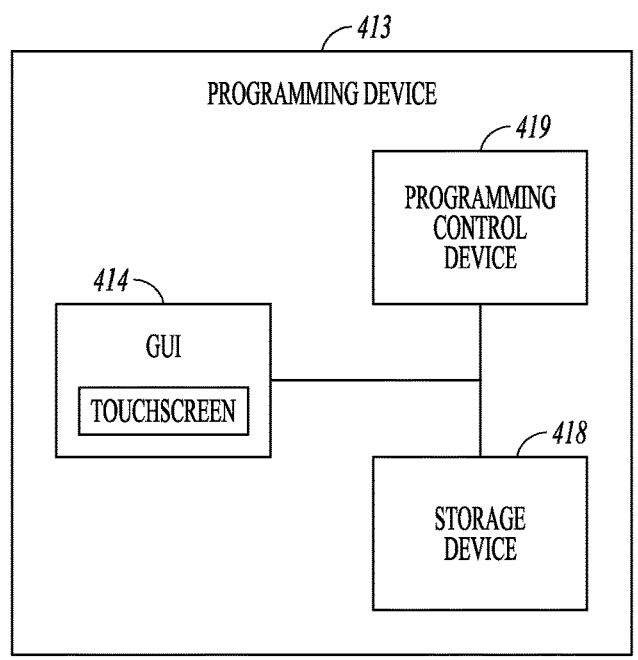
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The programming device 413 may transmit the plurality of modulation parameters to the modulation device. In some embodiments, the programming device 413 may transmit power to the modulation device. The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
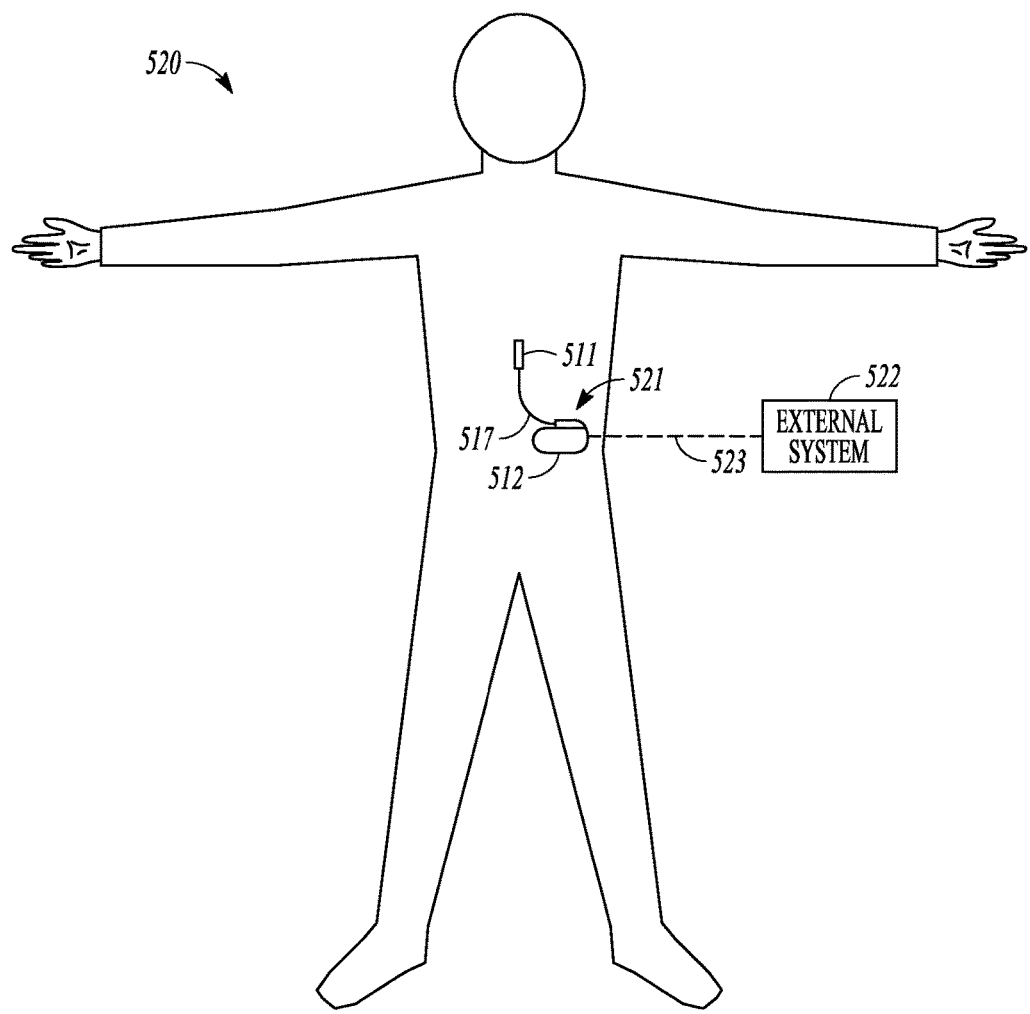
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets such as may be useful for delivering other therapies. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable modulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
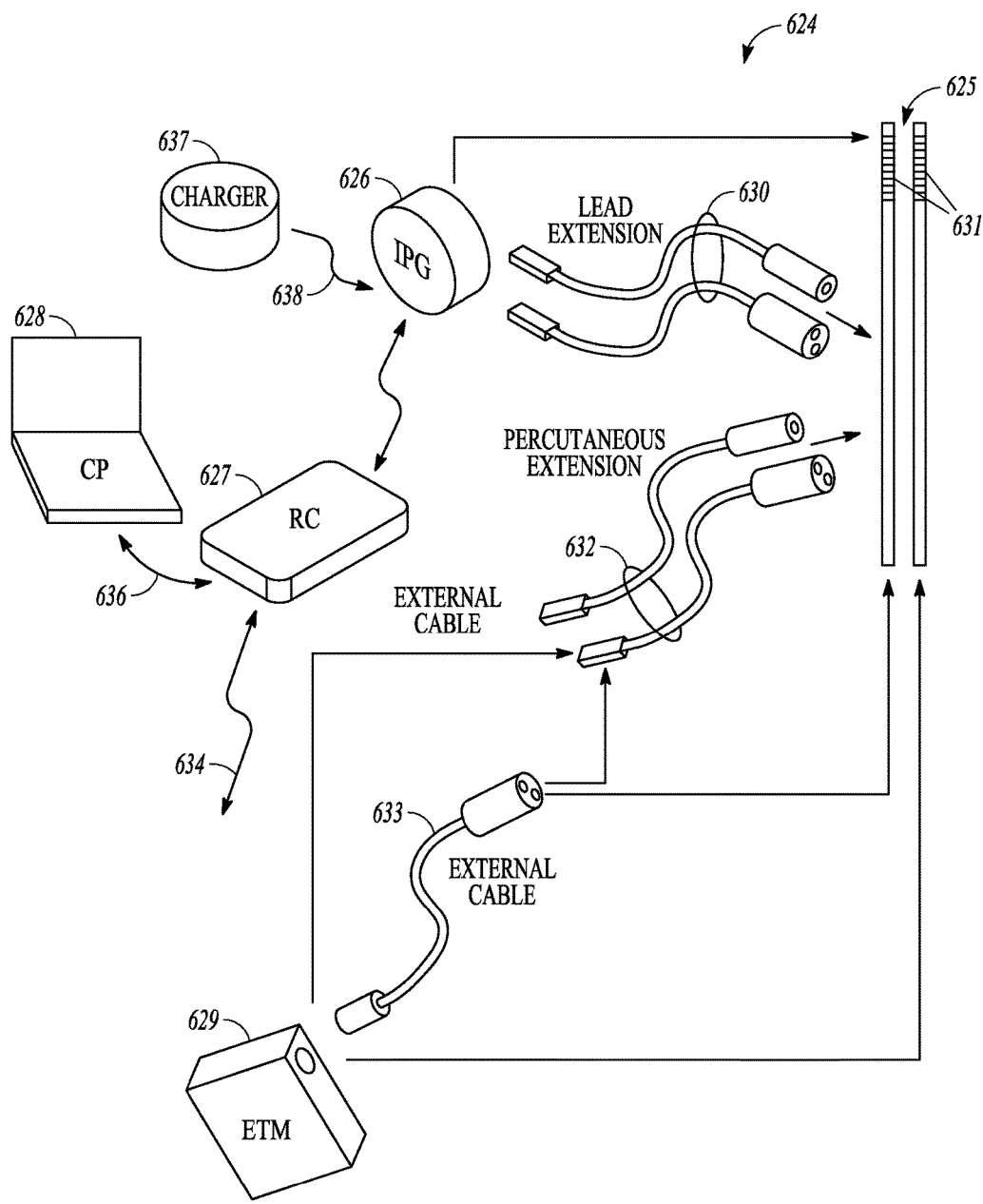
FIG. 6 illustrates, by way of example, an embodiment of a Spinal Cord Stimulation (SCS) system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 624 may generally include a plurality (illustrated as two) of implantable neuromodulation leads 625, an implantable pulse generator (IPG) 626, an external remote controller RC 627, a clinician's programmer (CP) 628, and an external trial modulator (ETM) 629. The IPG 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 626 includes pulse generation circuitry, also referred to as a pulse generator, that delivers electrical modulation energy in the form of a pulsed electrical waveform (i.e., a temporal series of electrical pulses) to the electrodes in accordance with a set of modulation parameters.

The ETM 629 may also be physically connected via the percutaneous lead extensions 632 and external cable 633 to the neuromodulation leads 625. The ETM 629 may have similar pulse generation circuitry as the IPG 626 to deliver electrical modulation energy to the electrodes accordance with a set of modulation parameters. The ETM 629 is a non-implantable device that is used on a trial basis after the neuromodulation leads 625 have been implanted and prior to implantation of the IPG 626, to test the responsiveness of the modulation that is to be provided. Functions described herein with respect to the IPG 626 can likewise be performed with respect to the ETM 629.

The RC 627 may be used to telemetrically control the ETM 629 via a bi-directional RF communications link 634. The RC 627 may be used to telemetrically control the IPG 626 via a bi-directional RF communications link 635. Such control allows the IPG 626 to be turned on or off and to be programmed with different modulation parameter sets. The IPG 626 may also be operated to modify the programmed modulation parameters to actively control the characteristics of the electrical modulation energy output by the IPG 626. A clinician may use the CP 628 to program modulation parameters into the IPG 626 and ETM 629 in the operating room and in follow-up sessions.

The CP 628 may indirectly communicate with the IPG 626 or ETM 629, through the RC 627, via an IR communications link 636 or other link. The CP 628 may directly communicate with the IPG 626 or ETM 629 via an RF communications link or other link (not shown). The clinician detailed modulation parameters provided by the CP 628 may also be used to program the RC 627, so that the modulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical modulation generated by the IPG 626 to allow the desired parameters to be determined based on patient feedback or other feedback and for subsequently programming the IPG 626 with the desired modulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting.

An external charger 637 may be a portable device used to transcutaneously charge the IPG via a wireless link such as an inductive link 638. Once the IPG has been programmed, and its power source has been charged by the external charger or otherwise replenished, the IPG may function as programmed without the RC or CP being present.

Figure 7:
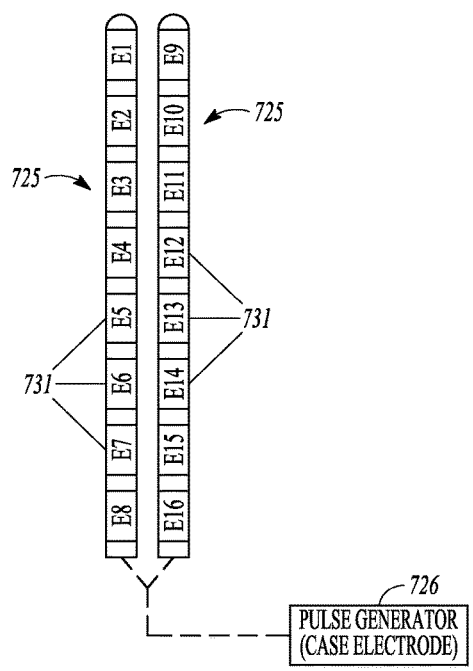
FIG. 7 illustrates, by way of example, some features of the neuromodulation leads and a pulse generator.

FIG. 7 illustrates, by way of example, some features of the neuromodulation leads 725 and a pulse generator 726. The pulse generator 726 may be an implantable device (IPG) or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by IPG.

Electrical modulation energy is provided to the electrodes in accordance with a set of modulation parameters programmed into the pulse generator. The electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). The electrical pulse parameters may define an intermittent modulation with "on" periods of time where a train of two or more pulses are delivered and "off" periods of time where pulses are not delivered. Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the IPG case. The system may be capable of transmitting modulation energy to the tissue in a monopolar or multipolar (e.g., bipolar, tripolar, etc.) fashion. Monopolar modulation occurs when a selected one of the lead electrodes is activated along with the case of the IPG, so that modulation energy is transmitted between the selected electrode and case.

Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia). Some embodiments may use one channel to prime the neural tissue with a sub-perception modulation field, and use another channel to deliver therapeutic sub-perception modulation to the neural tissue.

The IPG may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

Figures 8, 9:
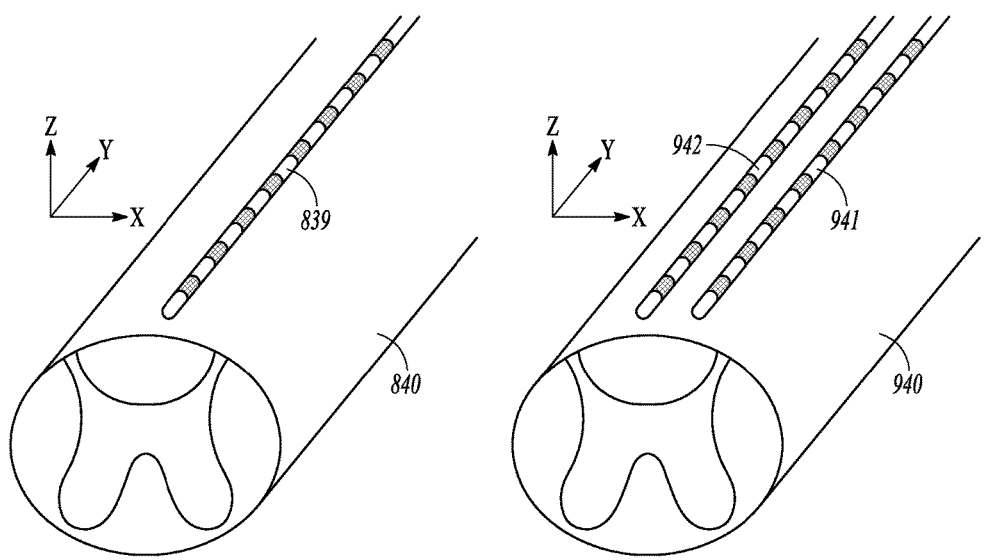
FIG. 8 is a schematic view of a single electrical modulation lead implanted over approximately the longitudinal midline of the patient's spinal cord.
FIG. 9 illustrates an embodiment where an electrical modulation lead has been implanted more laterally with respect to the spinal cord, thereby placing it proximate the dorsal horn of the spinal cord, and the other electrical modulation lead has been implanted more medially with respect to the spinal cord, thereby placing it proximate the dorsal column of the spinal cord.

FIG. 8 is a schematic view of a single electrical modulation lead 839 implanted over approximately the longitudinal midline of the patient's spinal cord 840. FIG. 9 illustrates an embodiment where an electrical modulation lead 941 has been implanted more laterally with respect to the spinal cord, thereby placing it proximate the dorsal horn of the spinal cord, and the other electrical modulation lead 942 has been implanted more medially with respect to the spinal cord, thereby placing it proximate the dorsal column of the spinal cord 940.

It is understood that additional leads or lead paddle(s) may be used, such as may be used to provide a wider electrode arrangement and/or to provide the electrodes closer to dorsal horn elements, and that these electrode arrays also may implement fractionalized current.

Placement of the lead more proximate to the DH than the DC may be desirable to preferentially stimulate DH elements over DC neural elements for a sub-perception therapy. Lead placement may also enable preferential modulation of dorsal roots over other neural elements. Any other plurality of leads or a multiple column paddle lead can also be used. Longitudinal component of the electrical field is directed along the y-axis depicted in FIG. 8, and a transverse component of the electrical field is directed along the x-axis depicted in FIG. 8.

Figure 10:
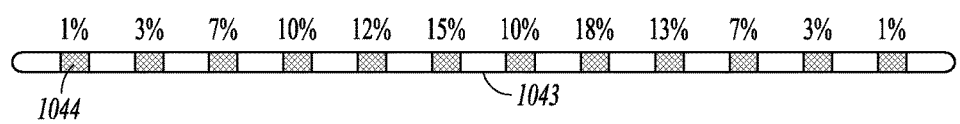
FIG. 10 illustrates a schematic view of the electrical modulation lead showing an example of the fractionalization of the anodic current delivered to the electrodes on the electrical modulation lead.

FIG. 10 is a schematic view of the electrical modulation lead 1043 showing an example of the fractionalization of the anodic current delivered to the electrodes on the electrical modulation lead. These figures illustrate fractionalization using monopolar modulation where a case electrode of the IPG is the only cathode, and carries 100% of the cathodic current. The fractionalization of the anodic current shown in FIG. 10 does not deliver an equal amount of current to each electrode 1044, because this embodiment takes into account electrode/tissue coupling differences, which are the differences in how the tissue underlying each electrode reacts to electrical modulation. Also, the ends of the portion of the electrical modulation lead include electrodes having lower gradient in the longitudinal direction. The magnitude of the electrical field tapers down at the ends of the electrical modulation lead. Fractionalization of the current may accommodate variation in the tissue underlying those electrodes. The fractionalization across the electrical modulation lead can vary in any manner as long as the total of fractionalized currents equals 100%. Various embodiments described herein implement a programmed algorithm to determine the appropriate fractionalization to achieve a desired modulation field property.

Modulation thresholds vary from patient to patient and from electrode to electrode within a patient. An electrode/tissue coupling calibration of the electrodes may be performed to account for these different modulation thresholds and provide a more accurate fractionalization of the current between electrodes. For example, perception threshold may be used to normalize the electrodes. The RC or the CP may be configured to prompt the patient to actuate a control element, once paresthesia is perceived by the patient. In response to this user input, the RC or the CP may be configured to respond to this user input by storing the modulation signal strength of the electrical pulse train delivered when the control element is actuated. Other sensed parameter or patient-perceived modulation values (e.g. constant paresthesia, or maximum tolerable paresthesia) may be used to provide the electrode/tissue coupling calibration of the electrodes.

The SCS system may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

Some embodiments are configured to determine a modulation parameter set to create a field shape to provide a broad and uniform modulation field such as may be useful to prime targeted neural tissue with sub-perception modulation. Some embodiments are configured to determine a modulation parameter set to create a field shape to reduce or minimize modulation of non-targeted tissue (e.g. DC tissue). Various embodiments disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of DH neural tissue and to minimize the modulation of DC tissue. A benefit of MICC is that MICC accounts for various in electrode-tissue coupling efficiency and perception threshold at each individual contact, so that "hot-spot" stimulation is eliminated.

Sub-perception SCS typically does not provide a quick feedback response regarding the effectiveness of the therapy. Rather, it has been observed that a wash-in period (a period of time for a delivered therapy to be therapeutically effective) for the sub-perception SCS is typically about one day. Thus, when the programmed modulation parameters are changed to change the location of the sub-perception modulation field, the patient may not be able to determine the effect that the changes have (e.g. pain relief) for a day or so. This make it difficult quickly titrate the modulation field of the sub-perception SCS to provide effective pain relief to the patient.

It has been observed during research that priming the neural tissue enables faster pain relief feedback from the patient during the search for the modulation field sweet spot. It may be appropriate to consider that priming the neural tissue "warms up" the neural tissue in a manner that reduces the wash-in time. However, neural physiology is complex and it is not currently understood why the primed neural tissue reduces the wash-in time of the sub-perception therapy such that the patient can quickly feel pain relief. It is noted that "priming" is different than conditioning pre-pulses which are delivered immediately before the neuromodulation pulse. A conditioning pre-pulse is timed to make a nerve more susceptible or less susceptible to capture by the immediately subsequent neuromodulation pulse. Thus, a conditioning pre-pulse as a specific relationship to a neuromodulation pulse. In contrast, the prime modulation field extends over a much longer period of time. Further, rather than making neural tissue more or less excitable by a pulse, the prime modulation field reduces a wash-in time of a therapy to make a patient feel the effects of the therapy (e.g. pain relief) much more quickly than would be felt without the prime field.

Various embodiments may deliver a low intensity, modulation field in preparation to test for and find the sweet-spot for the modulation field. The preparatory, lower intensity field is referred to herein as a prime field, as it is used to prime the neural tissue to be tested to have a quicker response to during the testing for the modulation sweet spot for pain relief. The prime field can be a supra-perception or sub-perception modulation field, but is typically even lower than the therapeutic sub-perception modulation field.

A test region of neural tissue represents a region of tissue that is to be tested for a sweet spot. The test region may include many potential locations for targeting the modulation field. The test region may span along the entire electrode arrangement (e.g. lead(s)) or may be reduced to a portion of the electrode arrangement. Priming may also be applied in a trolling fashion to cover the entire test region. As it is not known what location is to be most effective, the entire test region is primed.

In a non-limiting example to illustrate the lower intensity of the prime modulation field, one may assume that a patient may feel paresthesia or otherwise perceive the delivery of the modulation field when the modulation current has an amplitude of 10 mA. Thus, 10 mA may be considered to be a perception threshold for the modulation. Therapeutic sub-perception modulation maybe delivered within a range of 30% to 90% of the perception threshold. Thus, in this example, modulation with an amplitude between 3 mA and 9 mA may be therapeutically effective (e.g. provide pain relief). Priming the neural tissue may be accomplished using amplitudes near the lower range of the sub-perception modulation or even below the lower range of the sub-perception modulation such as, by way of example, between 2 mA to 4 mA. The sub-perception modulation affects the neural tissue, but not to the point where the modulation induces the nerve to trigger action potentials. Thus, the prime field may affect the ion concentrations within and outside of the neural pathways responsible for pain relief and/or may affect neurotransmitters responsible for pain relief, such that additional changes by sub-perception modulation may more quickly induce desirable action potentials in these neural pathways responsible for pain relief.

Figures 11A, 11B:
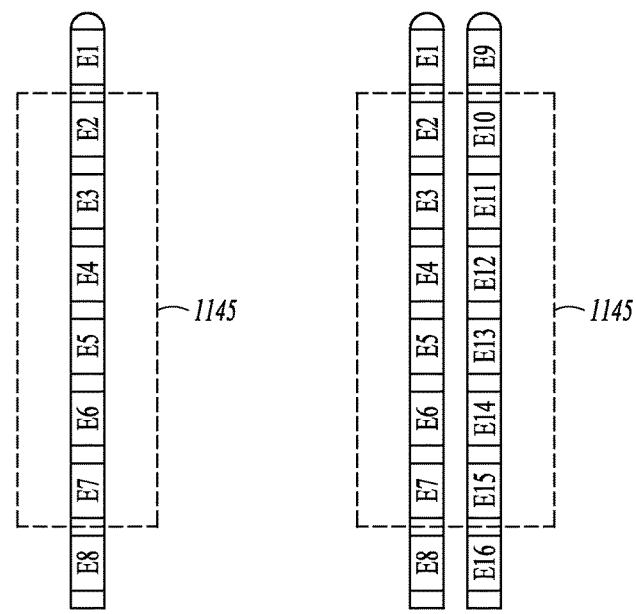
FIGS. 11A-11B illustrate, by way of example and not limitation, electrode arrangements and test regions of neural tissue along the electrode arrangements.

FIGS. 11A-11B illustrate, by way of example and not limitation, electrode arrangements (e.g. E1-E8 in FIG. 11A and E1-E16 in FIG. 11B) and test regions 1145 of neural tissue along the electrode arrangements. These test regions 1145 may extend across the entire electrode arrangement. In some embodiments, the test regions may extend along only a portion of the electrode arrangement. By way of example, some embodiments may allow a user to select the test region and thus select the portion of the electrode arrangement to be tested. In the example illustrated in FIG. 11A the test region is neural tissue along the E2 to E7 electrodes, and in the example illustrated in FIG. 11B the test region is neural tissue along the E2 through E7 and the E10 to E15 electrodes.

The electrodes in the electrode arrangement may be fractionalized, using different modulation parameter sets, to change the portion of the neural tissue that is modulated. Thus, there may be many neural tissue locations that can be targeted with the test region of neural tissue adjacent to the electrode arrangement. FIGS. 12A-12C illustrate, by way of example and not limitation, neural tissue locations 1246 that may be targeted within the test region in one, two and three dimensions, respectively. In the one-dimensional example illustrated in FIG. 12A, the neural locations that may be targeted may simply be a line of potential targets such as may be observed from a single lead with a linear arrangement of electrodes. In the two dimensional example illustrated in FIG. 12B the neural locations that may be targeted may be considered to lie in a plane proximate to the electrode arrangement. In the three-dimensional example illustrated in FIG. 12C, the neural locations that may be targeted may be considered to be a volume of tissue proximate to the electrode arrangement. By way of example, the two-dimensional and three-dimensional test regions may be implemented using two or more leads of electrodes. Thus, the test regions may be relatively simple or complex shapes, and may include relatively few or relatively many locations to be tested.

Figure 13:
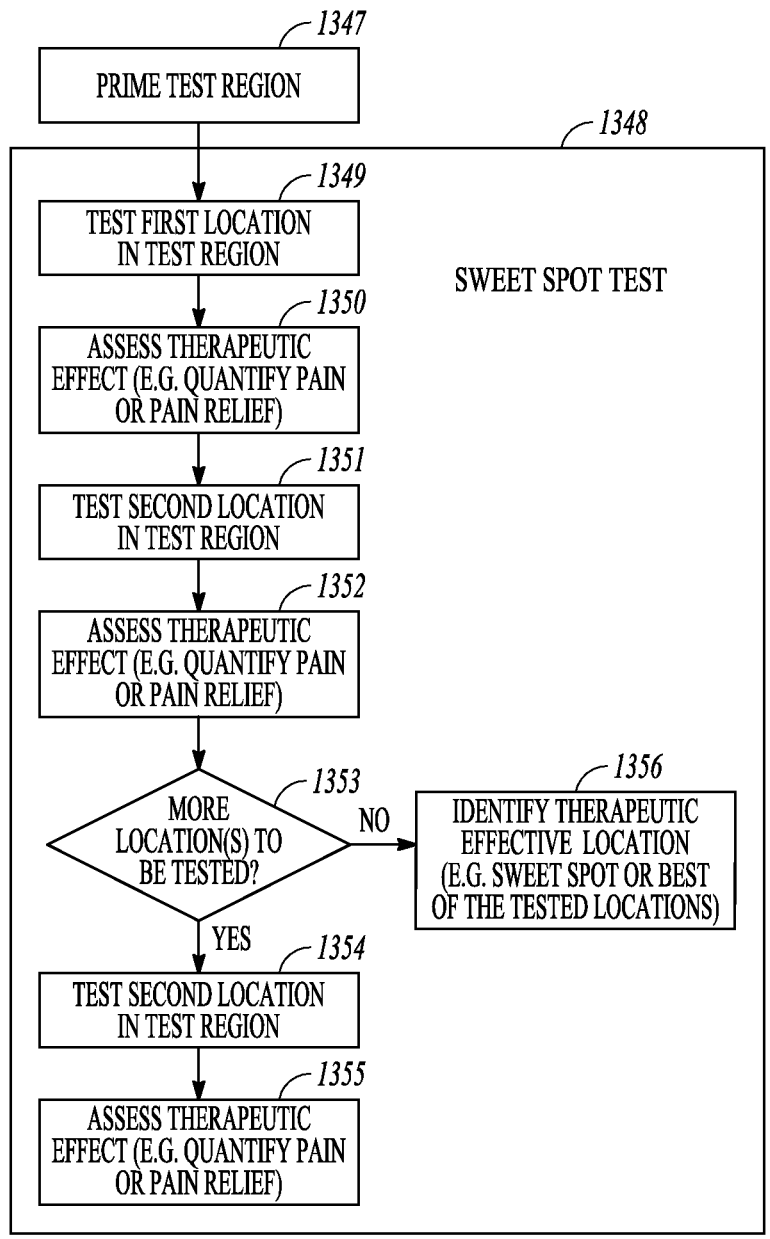
FIG. 13 illustrates an example of a method for finding a sweet spot for sub-perception modulation.

FIG. 13 illustrates an example of a method for finding a sweet spot for sub-perception modulation. In the illustrated example, a test region is primed with the sub-perception modulation field 1347, and the sweet-spot test is performed 1348 to find location of neural tissue that is therapeutically effective when targeted with sub-perception modulation. The sweet spot test may involve a manual process to reprogram the modulation field parameter set with different values to change the targeted location of the modulation field. In some embodiments of the test, the targeted location is automatically changed (e.g. trolled) by automatically changing values of the modulation field parameter set. Some embodiments may semi-automatically change values of the modulation field parameter set to change the targeted location of the modulation field.

At 1349, a first location in the test region is tested by focusing the modulation field onto the first location. At 1350, the therapeutic effect of modulating the first location is assessed. In an example where the therapy is a therapy to alleviate pain, the patient may provide this assessment by quantifying a level of pain or level of pain relief that they are experiencing. In some examples, a biomarker is used to provide an assessment of the therapeutic efficacy of the modulation field focused on the tested location. At 1351, the modulation field parameter set is changed to change the focus of the modulation field to test a second location in the test region. At 1352, the therapeutic effect of modulating the second location is assessed. If more location(s) are to be tested, as illustrated at 1353, the process may continue to 1354 to test the next location and to 1355 to assess the therapeutic effect of the next location. The process may determine or identify the location(s) that are therapeutically effective 1356 by evaluating the quantified effects of the therapy. In some embodiments, the quantified effects may be compared to each other to identify the tested location that has the best therapeutic effect (the sweet spot) or one of the best therapeutic effects (a sweet spot).

The present subject matter may be used to test relatively small locations using a more narrowly focused modulation field such as generally illustrated above in FIGS. 12A-12C, or may be used to test relatively larger locations of neural tissue using a more uniform (less focused) modulation field. The test of larger locations may be followed by a more focused test or tests within one of the larger location. Regardless of whether the test location is relatively large or relatively small, the present subject matter primes the test neural tissue to reduce a wash-in time of the therapy and enable a quick assessment of the effectiveness of the therapy. A few search algorithms are provided below as examples. Other processes for testing locations of neural tissue are possible.

Various embodiments start with full-lead then use a search algorithm to reduce the span and improve energy efficiency. This can be done from the RC or CP, or in the IPG with RC feedback. The proposed algorithms may rely on some form of feedback indicating the effectiveness of the modulation. For example, a patient may provide feedback regarding pain relief. Feedback may also provide a biomarker signal.

The system may include a routine to confirm that the modulation along the full lead is effective and then focus the modulation along a portion of the lead. Thus, for example, a generally uniform modulation field may be provided along this smaller portion of the lead. This field is still broad as it may be provided across an area with multiple electrode contacts, but it is less than the entire electrode arrangement using electrode array(s) on the lead(s).

Various embodiments may provide a rostra-caudal focus routine that includes a binary search routine. The binary search routine segments the lead or array of electrodes from a full set of electrodes into at least two subsets of electrodes that defines partial lead search regions. The binary search routine may confirm that modulation along the full lead is effective.

Figure 14:
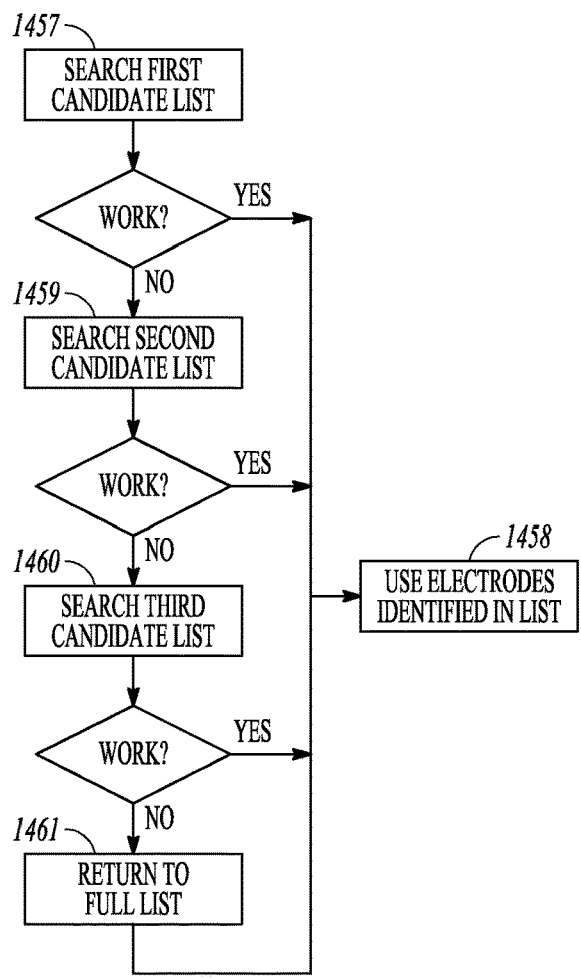
FIG. 14 illustrates, by way of example, aspects of a binary search routine as a rostra-caudal focus routine.

FIG. 14 illustrates, by way of example, aspects of a binary search routine as a rostra-caudal focus routine. A first subset of electrodes that define a first partial lead search region can be tested to determine if the modulation is effective using the first subset 1457. If it is effective, the first subset of electrodes that define the first partial lead search region may be used to deliver the modulation 1458 or for further more focused tests. If it is not effective, then a second subset of electrodes that define a second partial lead search region may be tested to determine if the second subset of electrodes is effective 1459. If it is effective, the second subset of electrodes that define the second partial lead search region may be used to deliver the modulation 1458. If it is not effective, then a third (or nth) subset of electrodes that define a third (or nth) partial lead search region may be tested to determine if the third (or nth) subset of electrodes is effective 1460. If it is effective, the third (or nth) subset of electrodes that define the third (or nth) partial lead search region may be used to deliver the modulation 1458. If it is not effective, then the binary search process may return to the full list of electrodes 1461 which was previously determined to be effective. At least some of the subsets of electrodes may be exclusive of each other. At least some of the subsets of electrodes may intersect with each other. In some embodiments, at least two subsets are exclusive, and at least one subset has an intersection with another subset.

Figure 15:
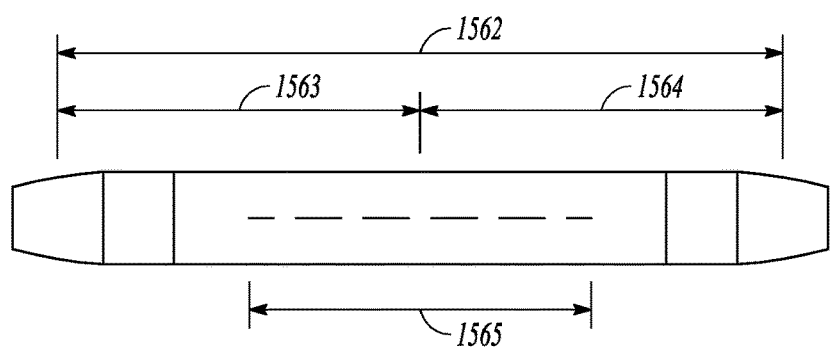
FIG. 15 illustrates an example of the binary search routine.

FIG. 15 illustrates an example of the binary search routine. The lead has a full span 1562 which may be split into three partial lead search regions 1563, 1564 and 1565, each partial search region including a corresponding subset of electrodes. By way of example and not limitation, the first and second subsets 1563 and 1564 of electrodes may be mutually exclusive, and third subset 1565 may include an intersection with the first subset and also may include an intersection with the second set. In an example, the full lead may be bifurcated to provide the first partial lead search region 1563 on a first side of the lead (e.g. left end of electrode array to middle) and the second partial lead search region 1564 on a second side of the lead (e.g. right end of the electrode array to middle). The third partial lead search region 1565 may partially overlap each of the first and second partial lead search regions. Thus, the partial lead search regions may define a first end region, a second end region and a middle region of the lead.

Figure 16A:
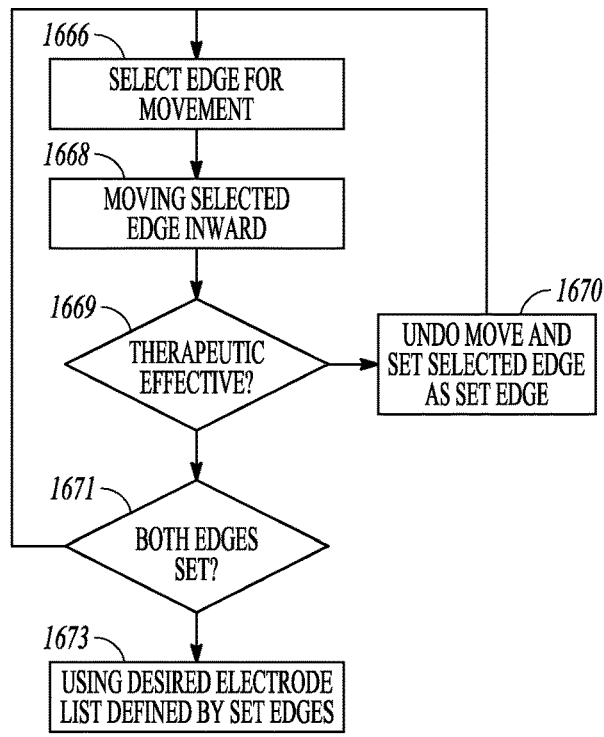
FIGS. 16A-16C illustrate, by way of example, an edge search routine.
Figure 16B:
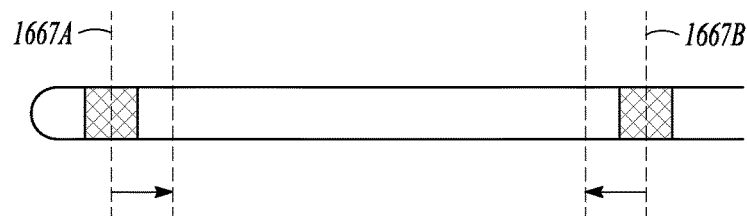
Figure 16C:
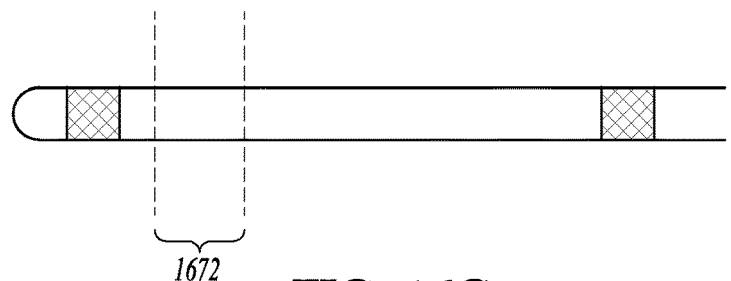

FIGS. 16A-16C illustrate, by way of example, an edge search routine. The edge search routine progressively moves each edge of the active electrodes in the array toward the middle and confirms that the modulation remains effective with the moves. Thus, a first edge can be moved toward the center until the next move toward the center causes the modulation to be ineffective; and a second edge can be moved toward the center until the next move toward the center causes the modulation to be ineffective.

For example, the edge search routine may include selecting an edge of the electrode arrangement (e.g. array) for movement 1666. The selected edge may be one of the two edges 1667A or 1667B illustrated in FIG. 16B. However, there can be more than two edges if more than two regions are being focused. The selected edge is moved inward 1668 toward the other edge for the region of interest. If the reduced set of electrodes is no longer therapeutically effective 1669, then the previous move can be undone and that edge can be set so that is no longer is capable of being selected for movement 1670. The process can return to 1666 to attempt to move the other edge(s). If the reduced set of electrodes continues to be therapeutically effective 1669, then the process returns to 1666 to continue moving edges until such time as all of the edges are set 1671. The final reduced set 1672 of electrodes can be used 1673 to deliver the modulation energy.

According to various embodiments, the programmed system may be configured with a neuromodulation focus routine such as a rostra-caudal focus routine to allow a user to select the desired electrodes for the neuromodulation to be more specific to the desired physiological area. Some embodiments may allow non-contiguous spans to be selected as a result of initial programming and/or neuromodulation refinement later on.

The modulation field may be moved from location to location using an automatic trolling process or through patient control. Candidate trolling algorithms include a monopolar troll (anodic or cathodic) or a bipolar troll or a multipolar troll. The troll can be done with MICC or multiple independent voltage control, or with a timing channel interleaving technique. MICC enables the locus of the modulation to be gradually moved across along the lead or within the array of electrodes. The interleaving of timing channels allows different electrode(s) in different timing channels. Values of stimulation parameter(s) (e.g. amplitude) in the timing channels can be adjusted. Thus by way of example and not limitation, if a monopolar modulation is delivered using a first electrode in a first channel and another monopolar modulation is delivered using a second electrode adjacent to the first electrode in a second channel, then the amplitude of the monopolar modulation in the first channel may be incrementally reduced as the amplitude of the monopolar modulation may be increase in the second channel. In this matter, the locus of the modulation may be gradually adjusted.

Various embodiments troll a modulation field, using an arrangement of electrodes on at least one lead, through neural tissue positions, and perform a quantification procedure multiple times as the modulation field is trolled through the positions. The quantification procedure identifies when the modulation field provides a therapeutic effect (e.g. pain relief). The quantification procedure may include receiving a marking signal that indicates that a modulation intensity achieved the therapeutic effect, and storing a value for the therapeutic effect as well as modulation field parameter data. The modulation intensity may include modulation parameters that affect the patient's perception of the modulation energy. These parameters may include pulse width, rate, amplitude, distribution of current, and electrode polarity (cathode v. anode). By way of example and not limitation, the storage of the parameter data may be in a temporary storage such as but not limited to cache or RAM or in permanent/persistent storage such as but not limited to ROM, a memory device such a hard drive, optical disc, thumb drive, or cloud storage. The quantification process may include receiving a titration signal that indicates an instruction to adjust modulation intensity, and adjusting the modulation intensity in response to receiving the titration signal. The titration signal may be initiated by a patient, or by a clinician or other user who is responding to patient responses.

Figure 17:
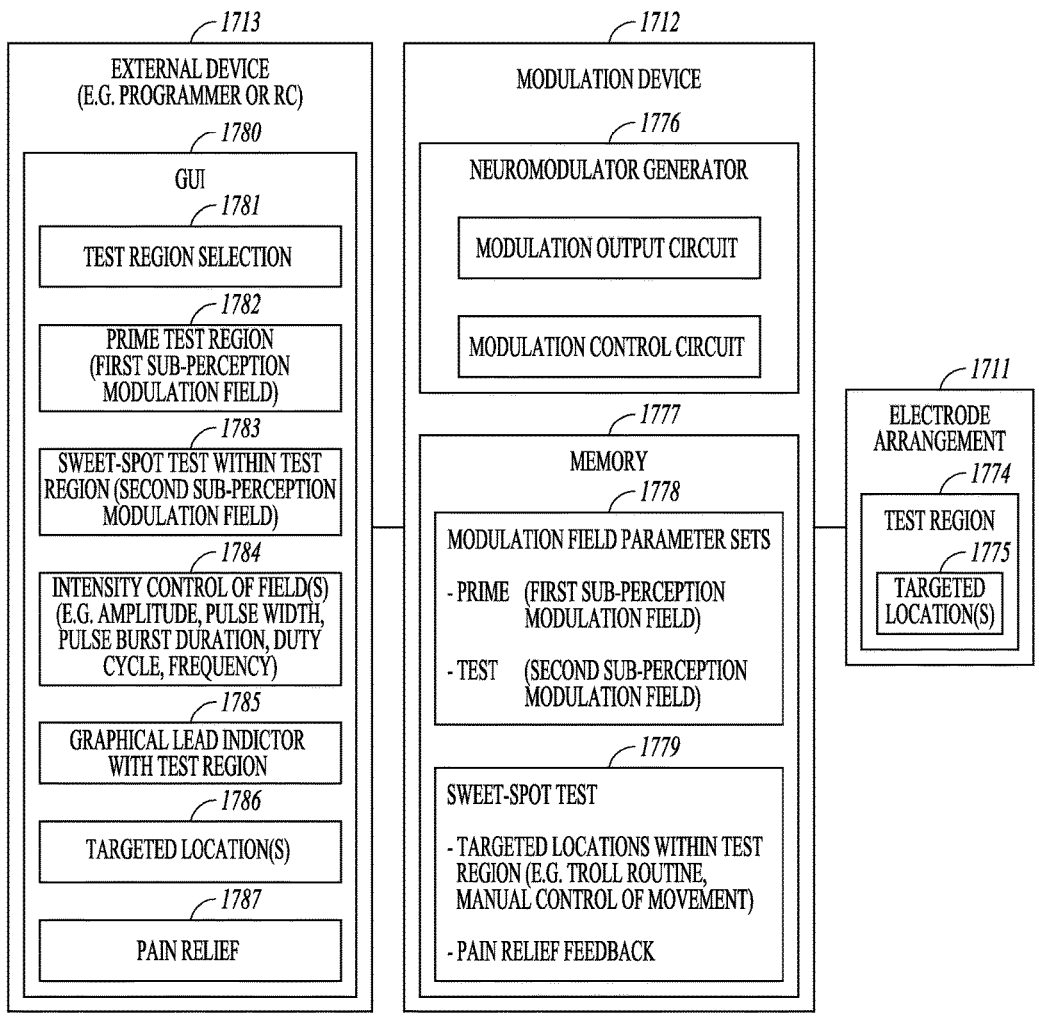
FIG. 17 illustrates an example of a system for finding a sweet-spot for sub-perception modulation.

FIG. 17 illustrates an example of a system for finding a sweet-spot for sub-perception modulation. The system may include an electrode arrangement 1711, a modulation device 1712, and an external device such as a programmer or remote control (RC) 1713. The illustrated electrode arrangement 1711 includes electrodes corresponding to a test region 1774 of neural tissue. The test region is proximate to the electrodes, and may be associated with all electrodes in the electrode arrangement or a subset of the electrodes in the electrode arrangement. The test region 1774 may include targeted location(s) 1775 which may be, as discussed above, a relatively focused small location or a relatively broad location.

The modulation device 1712 may include a neural modulator generator 1776 which may comprise a modulation output circuit and a modulation control circuit such as is generally illustrated in FIG. 3. The modulation device may further include memory 1777, which may include modulation field parameter sets 1778 and a sweet spot test routine 1779. The modulation field parameter sets may be used by the neuromodulator generator to control the modulation field generated by the electrode arrangement. The modulation field parameter sets may include a first sub-perception modulation field parameter set used by the neuromodulator generator to prime a test region, and include a second sub-perception modulation field parameter set used by the neuromodulator to test location(s) within the test region. The sweet spot test routine 1779 may include instructions for targeting location(s) within the test regions. The instructions for targeting location(s) may include instructions for receiving manual control inputs from a user or may include instructions for performing automated or semi-automated trolling of the movements. The sweet spot test routine 1779 may also include instructions for receiving feedback concerning the effective of the therapy. For example, the instructions may include instructions for receiving a quantification of the therapeutic effect (e.g. a pain rating) from the external device, and associating that quantification with the targeted location.

The external device 1713 may include a graphical user interface (GUI) 1780. Some embodiments of the GUI may provide test region selection element(s) 1781 used to select a test region. Some embodiments may also display the selected test region with respect to the electrode arrangement. Some embodiments of the GUI may include prime modulation element(s) 1782 used to program the first sub-perception modulation field parameter set that controls location and shape of the prime modulation field, and test element(s) 1783 used to program the second sub-perception modulation filed parameter set that controls location and shape of the second modulation field used in performing the sweet spot test. Some embodiments of the GUI may include an intensity control element(s) 1784 configured for use by the user to control the intensity of the first and/or second sub-perception modulation fields. The intensity of the stimulation maybe controlled by controlling an amplitude of the modulation pulses. In addition or as an alternative, the intensity of the stimulation may be controlled by controlling a pulse with of the modulation pulses, the pulse burst duration, the duty cycle of the pulses, the burst on/burst off duty cycle and/or pulse frequency of the modulation pulses. Some GUI embodiments provide an element to provide an indicator 1785 of a graphical lead with a test region identified in relative position with respect to the illustrated lead. Some embodiments may allow the user to set or adjust the test region, such as by dragging illustrated boundaries of the test region on the GUI. Some GUI embodiments provide an element 1786 to provide an indicator of targeted location(s) within a test region, and some embodiments may allow the user to set or adjust the targeted location(s). A GUI example may include element(s) 1787 to allow a user to enter feedback regarding the effective of the therapy. For example, the feedback may be a quantification of pain or pain relief.

Figure 18:
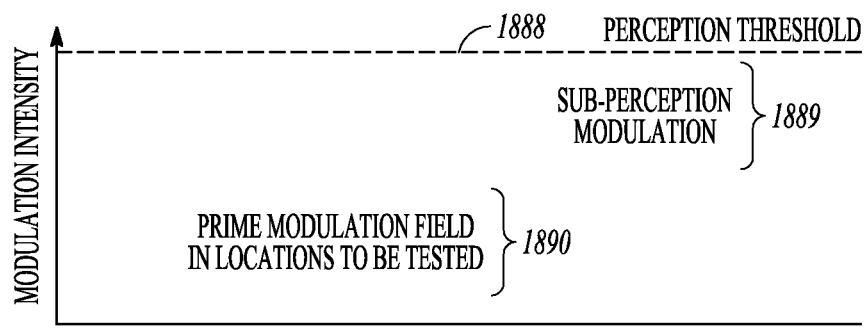
FIG. 18 illustrates, by way of example, and not limitation, sub-perception modulation intensity used to prime the test region and to test a therapeutic effect of locations within the test region.

FIG. 18 illustrates, by way of example, and not limitation, sub-perception modulation intensity used to prime the test region and to test a therapeutic effect of locations within the test region. The perception threshold 1888 illustrates the intensity of the modulation field at the boundary between perceptible modulation and sub-perception modulation. Perceptible modulation is where the modulation field delivers energy that is perceptible to the patient. Examples of perceptible stimulation include stimulation that causes paresthesia. Perceptible modulation may also include modulation that causes a temperature change or a motor response. The therapeutic sub-perception modulation 1889 is therapeutically effective, even though the delivery of the modulation energy is not perceived by the patient. As discussed earlier, the perception threshold may be different for different portions of the electrode arrangement. Some embodiments calibrate the modulation to account for these differences. The prime sub-perception modulation 1890 is generally at a lower energy than the sub-perception modulation 1889.

Figure 19A:
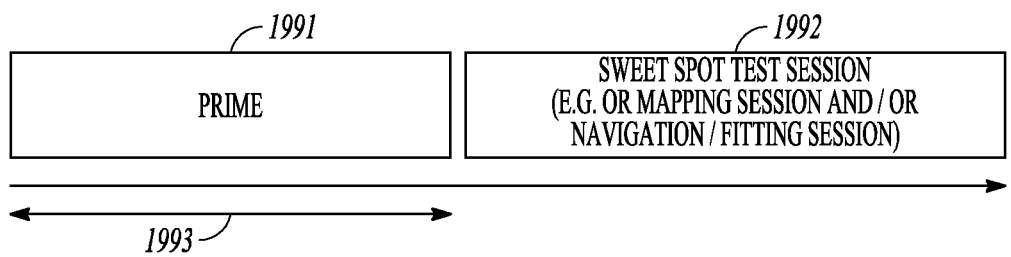
FIGS. 19A-19B illustrate relative timing between the prime modulation field and the sweet spot test session to test a therapeutic effect of locations within the test region.
Figure 19B:
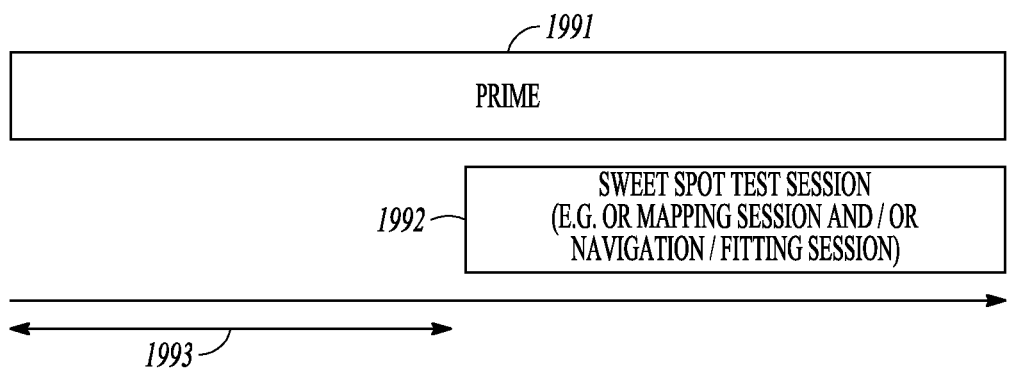

FIGS. 19A-19B illustrate relative timing between the prime modulation field 1991 and the sweet spot test session 1992 to test a therapeutic effect of locations within the test region. In both examples, the prime modulation field 1991 is delivered for a time period 1993 before the sweet spot test session 1992. For example, this time period 1993 may be more than 30 minutes. In some embodiments, this time period 1993 is more than an hour. In some embodiments the time period 1993 is more than 6 hours and less than a week. In some embodiments, the time period 1993 is longer than 1 day and shorter than 3 days. In the embodiment illustrated in FIG. 19A, the prime modulation field 1991 is stopped before the sweet spot test session 1992 begins. There may be a time period 1994 between the prime modulation field and the sweet spot test session without any modulation. In some embodiments, the prime-modulation field continues during at least a portion of the sweet spot test session. FIG. 19B illustrates an example in which the sweet spot test session 1992 is performed while the prime modulation field 1991 is generated. The sweet spot test session may be performed during an operation room mapping session and/or during a navigation fitting session.

In addition to the Examples discussed in the Summary Section above, some other non-limiting examples are provided as follows.

An example (e.g., "Example 26") of a system includes an electrode arrangement, a neuromodulation generator, a memory, and a controller. The neuromodulation generator may be configured to use electrodes in the electrode arrangement to generate modulation fields. The modulation fields may include a first sub-perception modulation field over a test region of neural tissue along the electrode arrangement to prime the neural tissue throughout the test region and a second sub-perception modulation field to test a plurality of targeted locations of neural tissue within the test region for therapeutic effectiveness. The memory may be configured to store a first modulation field parameter set for use to generate the first sub-perception modulation field, and a second modulation field parameter set for use to generate the second sub-perception modulation field to modulate one targeted region of the plurality of the targeted locations within the test region. The second modulation field parameter set may be programmable to change the second sub-perception modulation field to modulate other ones of the plurality of targeted locations. The controller may be configured to control the neuromodulation generator to use the first modulation field parameter set to prime the test region with the first sub-perception modulation field and to use the second modulation field parameter set to deliver a second sub-perception modulation field to modulate the one of the targeted locations within the test region.

In Example 27, the subject matter of Example 26 may optionally be configured such that the controller is configured to generate the first sub-perception modulation field to prime the test region for a period of time before the second sub-perception modulation field.

In Example 28, the subject matter of Example 27 may optionally be configured such that the period of time is over 30 minutes.

In Example 29, the subject matter of Example 28 may optionally be configured such that the period of time is between one hour and one week.

In Example 30, the subject matter of any one or any combination of Examples 27-29 may optionally be configured such that the controller is configured to stop generating the first sub-perception modulation field before generating the second sub-perception modulation field.

In Example 31, the subject matter of any one or any combination of Examples 27-29 may optionally be configured such that the controller is configured to generate the first sub-perception modulation field for at least a portion of a time when the second sub-perception modulation field is generated.

In Example 32, the subject matter of any one or any combination of Examples 26-31 may optionally be configured such that the controller is configured to implement a trolling routine to troll the second sub-perception modulation field through the plurality of targeted locations within the test region of neural tissue.

In Example 33, the subject matter of Example 32 may optionally be configured such that the trolling routine implemented by the controller is configured to perform at least one of automatically moving the second sub-perception modulation field or receiving a user-controlled trolling command to control movement of the second sub-perception modulation field.

In Example 34, the subject matter of Example 33 may optionally be configured such that the programmable second modulation field parameter set includes programmable fractionalized current values for electrodes within the electrode arrangement, and modification of the programmable fractionalized current values moves the second sub-perception modulation field.

In Example 35, the subject matter of any one or any combination of Examples 32-34 may optionally be configured such that the controller is configured to implement a routine as the second sub-perception modulation field is trolled through the plurality of targeted positions within the test region to identify a therapeutically-effective location in the test region where the second sub-perception modulation field provides pain relief, and to store in the memory the modulation field parameter data that provides the pain relief as the second modulation field parameter set.

In Example 36, the subject matter of Example 35 may optionally be configured such that the therapeutically-effective location is a tested location within the test region of neural tissue that is most effective in providing pain relief.

In Example 37, the subject matter of any one or any combination of Examples 35-36 may optionally be configured such that the routine implemented by the controller is configured to receive a titration signal that indicates an instruction to adjust an intensity of the second sub-perception modulation field, adjust the intensity in response to receiving the titration signal, and receive an indication signal that the adjusted modulation intensity achieved the pain relief.

In Example 38, the subject matter of Example 37 may optionally be configured such that the titration signal includes an automatically-provided signal to automatically adjust the intensity of the second sub-perception modulation field. The system may be configured to receive a user-provided command to stop the automatic adjustment of the intensity of the second sub-perception modulation field.

In Example 39, the subject matter of any one or any combination of Examples 26-38 may optionally be configured such that the controller is configured to use a timing channel to prime the test region and to use at least one other timing channel to generate to deliver the therapeutic sub-perception modulation.

In Example 40, the subject matter of any one or any combination of Examples 26-39 may optionally be configured such that the system includes an implantable device and an external device. The implantable device includes the neuromodulation generator, the memory and the controller. The external device and the implantable device are configured to communicate. The external device is configured to provide a graphical user interface to provide at least one of: a graphical lead indicator configured to indicate the test region of neural tissue and at least one targeted region of the plurality of the targeted locations within the test region.

An example of a method (e.g., "Example 41") is also provided. The method may include generating a first sub-perception modulation field over a test region of neural tissue along an electrode arrangement to prime the neural tissue throughout the test region, and generating a second modulation field to test a plurality of targeted locations of neural tissue within the test region for therapeutic effectiveness.

In Example 42, the subject matter of generating the first sub-perception modulation field as found in Example 41 may optionally include generating the first sub-perception modulation field over the test region of neural tissue along the electrode arrangement to prime the neural tissue throughout the test region for a period of time before generating the second sub-perception modulation field.

In Example 43, the subject matter of the period of time as found in Example 42 may optionally include that the period of time is over 30 minutes.

In Example 44, the subject matter of any one or any combination of Examples 42-43 may optionally further include stopping the first sub-perception modulation field before generating the second sub-perception modulation field.

In Example 45, the subject matter of generating the first sub-perception modulation field as found in any one or any combination of Examples 42-43 may optionally include generating the first sub-perception modulation field for at least a portion of a time when the second sub-perception modulation field is generated.

In Example 46, the subject matter of any one or any combination of Examples 41-45 may optionally further include trolling the second sub-perception modulation field through the plurality of targeted locations within the test region of neural tissue. The trolling includes automatically moving the second sub-perception modulation field, or receiving a user-controlled trolling command to control movement of the second sub-perception modulation field.

In Example 47, the subject matter of generating the second sub-perception modulation field as found in any one or any combination of Examples 41-46 may optionally include using a programmable second modulation field parameter set to generate the second sub-perception modulation field to modulate one of the plurality of targeted locations within the test region.

In Example 48, the subject matter of Example 47 may optionally further include programming different values for the programmable second modulation field parameter set to move the second sub-perception modulation field to different ones of the plurality of targeted locations within the test region of neural tissue.

In Example 49, the subject matter of any one or any combination of Examples 41-48 may optionally further include implementing a routine to identify a therapeutically-effective location in the test region where the modulation field provides pain relief, and programming the modulation field parameter data that provides the pain relief as the second modulation field parameter set.

In Example 50, the subject matter of implementing the routine to identify the therapeutically-effective location as found in Example 49 may optionally include identifying a tested location within the test region of neural tissue that is most effective in providing pain relief.

The above detailed description is intended to be illustrative, and not restrictive. The scope of the disclosure should, therefore, be determined with references to the appended claims, along with the full scope of equivalents to which such claims are entitled.

What is claimed is:
1. A method, comprising:
generating a first modulation field over a test region of neural tissue along an electrode arrangement to prime the neural tissue throughout the test region; and
generating a second modulation field to test a plurality of targeted locations of neural tissue within the test region for therapeutic effectiveness, including using programmable fractionalized current values for electrodes of the electrode arrangement to move the second modulation field to one or more locations of the plurality of targeted locations, wherein each of the first modulation field and the second modulation field includes a sub-perception modulation field, generating the second modulating field comprises generating a second modulation current having an amplitude set between upper and lower values each specified as a percentage of a perception threshold, and generating the first modulating field comprises generating a first modulation current having an amplitude set to approximately the lower value.

2. The method of claim 1, wherein generating the first modulation field includes generating the first modulation field over the test region of neural tissue along the electrode arrangement to prime the neural tissue throughout the test region for a period of time before generating the second modulation field.

3. The method of claim 1, wherein generating the first modulation field includes generating the first modulation field for at least a portion of a time when the second modulation field is generated.

4. The method of claim 1, further comprising trolling the second modulation field through the plurality of targeted locations within the test region of neural tissue, wherein the trolling includes automatically moving the second modulation field or receiving a user-controlled trolling command to control movement of the second modulation field.

5. The method of claim 1, wherein generating the second modulation field includes using a programmable second modulation field parameter set to generate the second modulation field to modulate each location of the plurality of the targeted locations within the test region, the programmable second modulation field parameter set including the programmable fractionalized current values for the electrodes of the electrode arrangement.

6. The method of claim 5, further comprising identifying one or more therapeutically-effective locations from the plurality of targeted locations where the second modulation field provides pain relief.

7. The method of claim 5, further comprising identifying a therapeutically-effective location being a tested location of the plurality of targeted locations within the test region of neural tissue that is most effective in treating a condition using a therapeutic modulation.

8. The method of claim 7, further comprising:
priming a target region over the identified therapeutically-effective location; and
delivering the therapeutic modulation to the identified therapeutically-effective location.

9. The method of claim 1, wherein generating the second modulation current comprises generating a current having an amplitude set within a range of 30% to 90% of the perception threshold.

10. A system, comprising:
an electrode arrangement;
a neuromodulation generator configured to use electrodes in the electrode arrangement to generate modulation fields including:

a first modulation field over a test region of neural tissue along the electrode arrangement to prime the neural tissue throughout the test region; and
a second modulation field to test a plurality of targeted locations of neural tissue within the test region for therapeutic effectiveness;
a memory configured to store a first modulation field parameter set for use to generate the first modulation field, and a second modulation field parameter set for use to generate the second modulation field to modulate one of the plurality of the targeted locations within the test region, the second modulation field parameter set including fractionalized current values for electrodes within the electrode arrangement that are programmable to change the second modulation field to modulate other ones of the plurality of targeted locations; and
a controller configured to control the neuromodulation generator to use the first modulation field parameter set to prime the test region with the first modulation field and to use the second modulation field parameter set to deliver a second modulation field to the one of the plurality of targeted locations within the test region,
wherein the neuromodulation generator is configured to use electrodes in the electrode arrangement to generate the first modulation field and the second modulation field each being a sub-perception modulation field, and the controller is configured to set a current amplitude of the second modulation field between upper and lower values each specified as a percentage of a perception threshold and to set a current amplitude of the first modulation field to approximately the lower value.

11. The system of claim 10, wherein the controller is configured to generate the first modulation field to prime the test region for a period of time before generating the second modulation field; or the controller is configured to generate the first modulation field for at least a portion of a time when the second modulation field is generated.

12. The system of claim 10, wherein the controller is configured to implement a trolling routine to troll the second modulation field through the plurality of targeted locations within the test region of neural tissue, wherein the trolling routine implemented by the controller is configured to perform at least one of automatically moving the second modulation field or receiving a user-controlled trolling command to control movement of the second modulation field.

13. The system of claim 12, wherein the controller is configured to implement a routine as the second modulation field is trolled through the plurality of targeted positions within the test region to identify one or more therapeutically-effective locations in the test region where the second modulation field provides pain relief, and to store in the memory the modulation field parameter data that provides the pain relief as the second modulation field parameter set and measures indicating therapeutic effectiveness for each location of the plurality of targeted positions.

14. The system of claim 13, wherein the one or more therapeutically-effective locations includes a tested location within the test region of neural tissue that is most effective in providing pain relief.

15. The system of claim 13, wherein the neuromodulation generator is configured to prime a target region over the therapeutically-effective location and deliver a therapeutic modulation to the therapeutically-effective location.

16. The system of claim 10, wherein:
the system includes an implantable device and an external device;
the implantable device includes the neuromodulation generator, the memory and the controller; and
the external device is configured to send commands to the implantable device and provide a graphical user interface, the graphical user interface to provide at least one of: a graphical lead indicator configured to indicate the test region of neural tissue and at least one of the plurality of the targeted locations within the test region.

17. The system of claim 10, wherein the controller is configured to set the current amplitude of the second modulation field within a range of 30% to 90% of the perception threshold.

18. A non-transitory machine-readable medium including instructions, which when executed by a machine, cause the machine to:
generate a first modulation field over a test region of neural tissue along an electrode arrangement to prime the neural tissue throughout the test region; and
generate a second modulation field to test a plurality of targeted locations of neural tissue within the test region for therapeutic effectiveness, including using programmable fractionalized current values for electrodes of the electrode arrangement to move the second modulation field to one or more locations of the plurality of targeted locations,
wherein the first modulation field and the second modulation field are each generated to be a sub-perception modulation field, the second modulation is generated with a current amplitude set between upper and lower values each specified as a percentage of a perception threshold, and the first modulation field is generated with a current amplitude set to approximately the lower value.

19. The non-transitory machine-readable medium of claim 18, wherein the second modulation field is generated with the current amplitude set between 30% and 90% of the perception threshold.

20. The non-transitory machine-readable medium of claim 18, wherein the second modulation field is generated with the current amplitude set to a value that is therapeutically effective for providing pain relief.

* * * * *